(12) United States Patent
Ferguson et al.

(10) Patent No.: US 9,867,691 B2
(45) Date of Patent: *Jan. 16, 2018

(54) CONTINUOUS LOOP ASSEMBLY

(71) Applicant: RIVERPOINT MEDICAL, LLC, Portland, OR (US)

(72) Inventors: Patrick Edward Ferguson, Portland, OR (US); Patrick Joseph Ferguson, Portland, OR (US); Aaron Joseph Sundholm, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 141 days.

This patent is subject to a terminal disclaimer.

(21) Appl. No.: 15/049,630

(22) Filed: Feb. 22, 2016

(65) Prior Publication Data

US 2016/0166375 A1 Jun. 16, 2016

Related U.S. Application Data

(63) Continuation of application No. 13/477,628, filed on May 22, 2012, now Pat. No. 9,357,990.

(51) Int. Cl.
*A61B 17/04* (2006.01)
*A61F 2/08* (2006.01)
*A61B 17/06* (2006.01)
*A61B 17/00* (2006.01)

(52) U.S. Cl.
CPC ........ *A61F 2/0811* (2013.01); *A61B 17/0401* (2013.01); *A61B 17/0483* (2013.01); *A61B 17/06166* (2013.01); *A61B 2017/00349* (2013.01); *A61B 2017/0404* (2013.01); *A61B 2017/0417* (2013.01); *A61B 2017/06185* (2013.01); *A61F 2002/0829* (2013.01); *A61F 2002/0852* (2013.01); *Y10T 29/49826* (2015.01)

(58) Field of Classification Search
CPC ........ A61B 17/0401; A61B 2017/0404; A61B 2017/06185; A61B 2017/04017
See application file for complete search history.

(56) References Cited

U.S. PATENT DOCUMENTS

| | | | |
|---|---|---|---|
| 6,533,802 B2 | 3/2003 | Bojarski et al. | |
| 9,357,990 B2 | 6/2016 | Ferguson et al. | |
| 2002/0052629 A1* | 5/2002 | Morgan | A61B 17/0401 606/232 |
| 2008/0177302 A1 | 7/2008 | Shurnas | |
| 2010/0268273 A1 | 10/2010 | Albertorio et al. | |
| 2011/0087280 A1 | 4/2011 | Albertorio | |
| 2012/0046746 A1* | 2/2012 | Konicek | A61F 2/08 623/13.14 |
| 2012/0123541 A1 | 5/2012 | Albertorio et al. | |

* cited by examiner

*Primary Examiner* — Corrine McDermott
*Assistant Examiner* — Joshua Levine
(74) *Attorney, Agent, or Firm* — Timothy E. Siegel Patent Law, PLLC; Timothy E. Siegel

(57) ABSTRACT

Fixation assemblies having a button captured by a continuous (i.e., closed) loop of thread, such as ultra high molecular weight polyethylene (UHMWPE) fiber are disclosed herein. Preferred assemblies are constructed such that the intact button cannot be detached from the continuous loop without breaking or opening the loop of fiber. The closed fiber advantageously contains at least one or two stitched, or otherwise secured or reinforced, sections positioned on the loop.

24 Claims, 4 Drawing Sheets

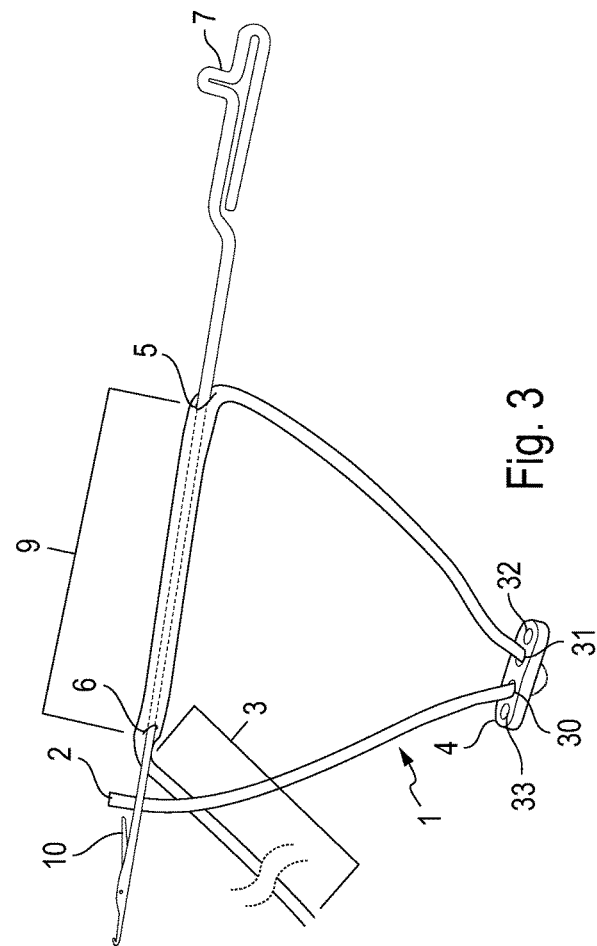
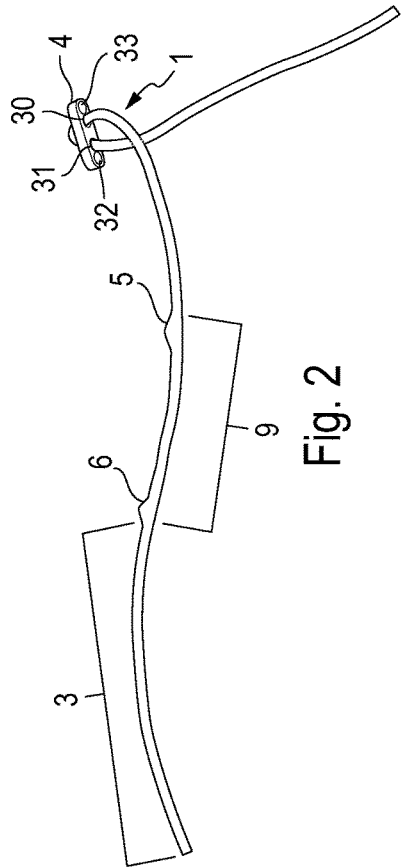
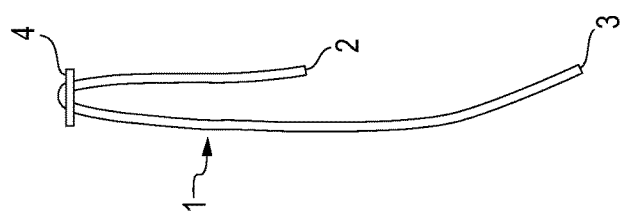

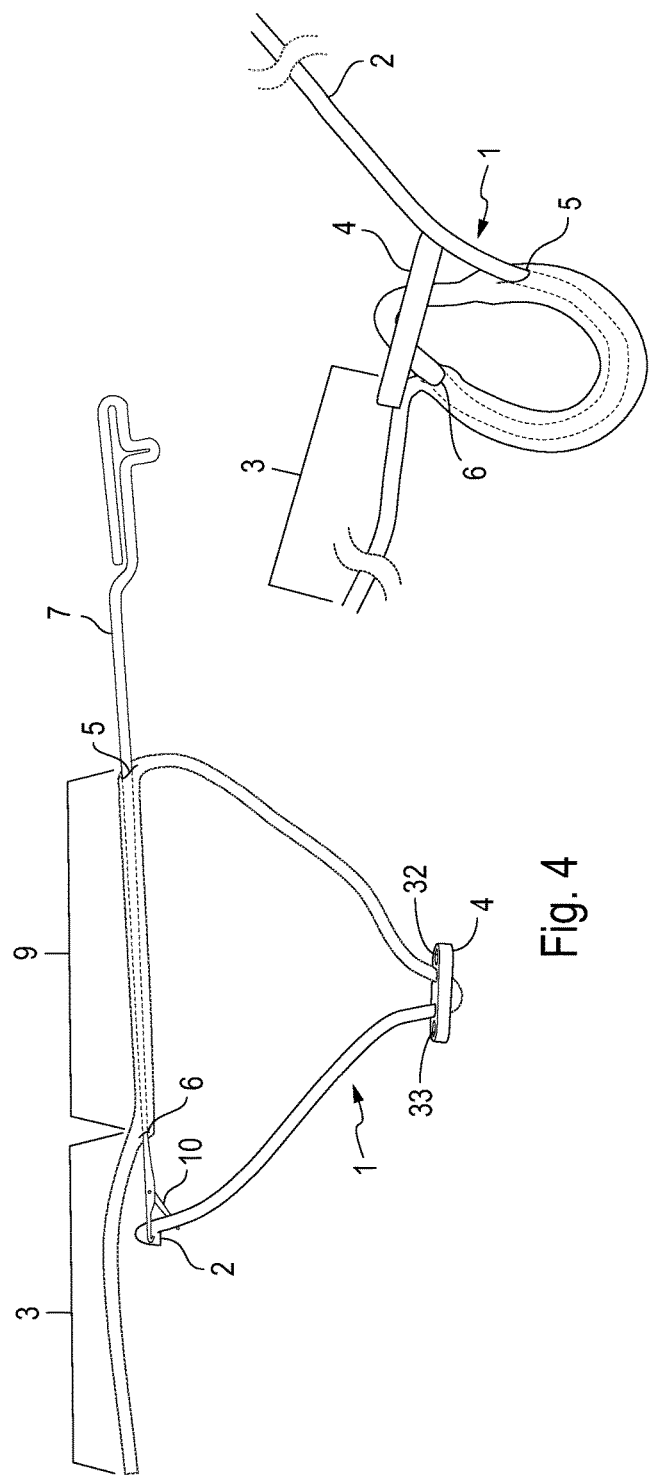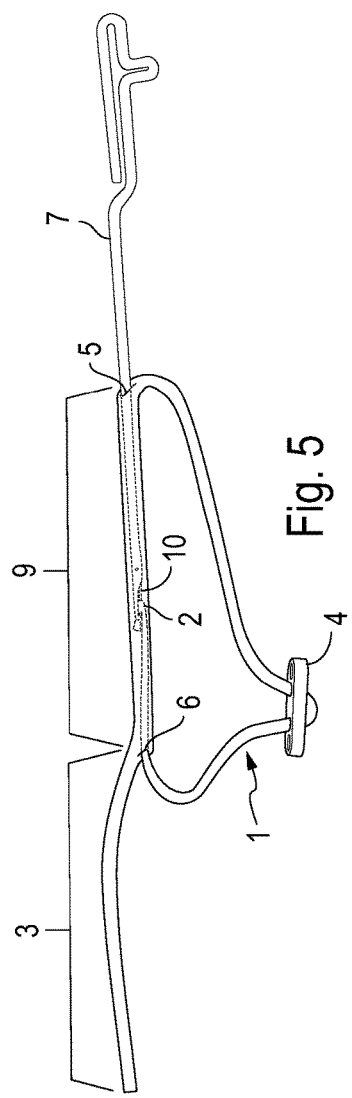

CONTINUOUS LOOP ASSEMBLY

RELATED APPLICATIONS

This application is a continuation of application Ser. No. 13/477,628 filed on May 22, 2012, which is incorporated by reference as if fully set forth herein.

FIELD OF THE INVENTION

The embodiments herein relate to bone-tendon-bone, single-bundle soft tissue, and double-bundle soft tissue fixation assemblies and methods of making and using said assemblies.

BACKGROUND

Continuous loop suture and button assemblies are commonly used during orthopedic surgery for bone-tendon-bone, single-bundle soft tissue, and double-bundle soft tissue fixation, such as during cruciate reconstruction. For example, during anterior cruciate ligament (ACL) reconstruction, a bone-tendon-bone graft is commonly positioned within both the femur and tibia bones. These grafts are often secured to a continuous loop/button assembly, which are in turn anchored to a bone. One example of a loop/button assembly is disclosed in U.S. Pat. No. 6,533,802 to Bojarski et al. ("Bojarksi"). Bojarski references a few different general methods of attaching a button to a continuous loop: (a) start with a closed loop suture and then capture the button by threading loop sections through openings in the button or wrapping the loop sections around channels/arms of the button (e.g., Bojarksi FIG. 12), (b) start with a thread having a leading end and utilize an automated winding machine to continuously wrap the leading end through apertures in the button to form a closed loop, such as disclosed in WO99/47079 to Bryant ("Bryant"), or (c) provide a suture with two open ends, thread and/or wrap the suture to an anchor button and then tie the open ends together, such as disclosed in U.S. Pat. No. 5,769,894 to Ferragamo ("Ferragamo"). The above described methods of making continuous loop and button assemblies result in products that are susceptible to breaking over time due to mechanical stress. In light of the disadvantages of the prior art loop/button products, it is an object of the teachings herein to provide continuous loop and button assemblies and methods of making the same that are mechanically stronger than prior products.

SUMMARY

The teachings herein are directed to methods of making a continuous loop fixation assembly comprising providing an anchor button having an aperture; threading an open fiber having a lumen through the aperture of the button thereby defining first and second sections of the fiber separated by the button, wherein the first fiber section comprises a cut tail and the second fiber section comprises a save tail; inserting the cut tail within the lumen of the fiber at a first position to form a loop; inserting the save tail within the lumen of the fiber at a second position; and reinforcing a first section of the loop that includes the first position where the cut tail was inserted into the lumen of the fiber.

Further embodiments are directed to methods of making a continuous loop fixation assembly comprising providing an anchor button having an aperture; threading an open fiber having a lumen through the aperture of the button thereby defining first and second sections of the fiber separated by the button, wherein the first fiber section comprises a cut tail and the second fiber section comprises a save tail; inserting the cut tail within the lumen of the fiber at a first position to form a loop; inserting the save tail within the lumen of the fiber at a second position; and reinforcing a first section of the loop that fixates the cut tail and the save tail together within the fiber.

Still additional embodiments are directed to implantable continuous loop assemblies for graft fixation comprising: an anchor button having an aperture; a closed loop of braided fiber having a lumen and first and second tail ends threaded into the lumen at first and second positions to create an overlapped loop, wherein the closed loop of braided fiber passes through the aperture of the anchor button, such that the intact anchor button cannot be removed from the closed loop of fiber without breaking the loop of fiber; and a first reinforced section of fiber covering the first position where the first tail end is threaded into the lumen.

Further embodiments are directed to implantable continuous loop assemblies for graft fixation comprising: an anchor button having an aperture; a closed loop of braided fiber having a lumen and first and second tail ends threaded into the lumen at first and second positions to create an overlapped loop, wherein the closed loop of braided fiber passes through the aperture of the anchor button, such that the intact anchor button cannot be removed from the closed loop of fiber without breaking the loop of fiber; and a first reinforced section of fiber that couples the first and second tail ends together within the lumen.

BRIEF DESCRIPTION OF THE DRAWINGS

It will be appreciated that the drawings are not necessarily to scale, with emphasis instead being placed on illustrating the various aspects and features of embodiments of the invention, in which:

FIG. 1 is a perspective view of a button captured by an open fiber having two tails: a save tail and a cut tail.

FIG. 2 is a perspective view showing defined entry and exit points on the fiber for a lacing tool.

FIG. 3 is a perspective, partially internal view showing a lacing tool being inserted through the fiber.

FIG. 4 is a perspective, partially internal view showing the lacing tool grabbing the cut tail.

FIG. 5 is a perspective, partially internal view showing the lacing tool pulling the cut tail through the fiber.

FIG. 6 is a perspective, partially internal view of the cut tail extending out of the fiber.

DETAILED DESCRIPTION OF THE ILLUSTRATED EMBODIMENTS

Embodiments of the present invention are described below with reference to the above described Figures. It is, however, expressly noted that the present invention is not limited to the embodiments depicted in the Figures, but rather the intention is that modifications that are apparent to the person skilled in the art and equivalents thereof are also included.

Figure 12:
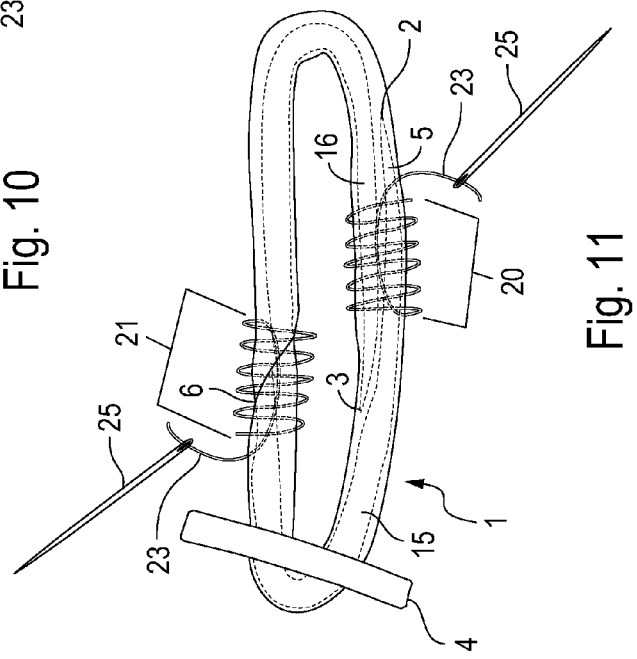
FIG. 12 is a perspective, partially internal view of the final continuous loop button assembly.

The teachings herein are primarily directed to a loop button assembly (e.g., 22) such as shown in FIG. 12 and methods of manufacturing the same. All materials present in the final assembly 22 should be biocompatible as a surgical implant, and are thus preferably sterilized, and packaged accordingly.

FIG. 1 is a perspective view of a button 4 coupled to an open fiber 1 having two tails: a save tail 3 and a cut tail 2. According to preferred embodiments, the fiber 1 is a biocompatible fiber, such as an ultra-high molecular weight polyethylene (UHMWPE) fiber, although suitable non-preferred materials can be used as well including polyester and POLYBLEND®, for example. Additionally, it is preferred that the fiber is braided as opposed to being monofilamentous. Braided fibers are particularly advantageous in the teachings herein as they are stronger and allow for the ends of the tails 3, 2 to be threaded through the fiber as will be discussed in more detail below.

The button 4 is coupled to the fiber 1 preferably through 1 or more apertures, (e.g., 30 and 31) in the button 4. Although the button 4 shown in the FIG. 2, includes two circular apertures 30 31 for feeding the fiber 1 through, and two additional circular apertures 32 33 for allowing the button to secure to additional sutures, or other coupling means such as to secure a bone-tendon-bone graft, this particular button design is expressly non-limiting. Any suitable number and shape of apertures can be used on an anchor button for the assemblies herein. Additionally, while the button 4 shown in FIG. 2 is racetrack shape any suitable shaped anchor button can be used with the loop assemblies provided herein. Non-limiting examples of buttons that can be used with the teachings herein, include the anchor of the XO BUTTON® commercially available by CONMED®/LINVATEC® and suitable buttons disclosed in U.S. Pat. No. 6,533,802 to Bojarski et al., and U.S. Pat. No. 5,306,301 to Graf et al., Thus the buttons used in the teachings herein can be a variety of shapes, nonexclusively including oval, racetrack, circular, square, rectangular, and can have 1, 2, 3, 4, 5, 6, or more apertures for allowing the continuous loop or additional sutures to be thread through. Apertures can be circular, ovular, square, rectangular, and the like as well. Additionally the button can include cantilevered arms defining channels, if so desired. Any of the above buttons are suitable in that they can couple to the continuous loop in a manner that an intact button cannot be detached from the loop without opening or breaking the loop.

Buttons are advantageously made from any suitable surgically implantable biocompatible material, non-exclusively including metal, including surgical steel and titanium, or thermoplastics, for example. Non-preferred buttons can be made of a biocompatible thermoplastic as well, for example.

With reference to FIGS. 1 and 2, the fiber 1 is threaded through apertures 30, 31 in the button 4. The button is then positioned approximately ⅓ down the length of the open fiber 1, thereby defining a ⅓ length section (having the cut tail 2) and a ⅔ length section (having the save tail 3). After the button 4 is situated about ⅓ down the length of the fiber 1, entry 5 and exit 6 points can be designated along the approximately ⅔ length section to define a middle section 9. The distal end of the ⅔ section, after the middle section 9, defines the save tail section 3. More specifically, preferred Table 1 can be utilized as an approximate guide to determine suitable lengths of the starting fiber 1, save tail 3, and middle section 9 based on the final loop size desired.

For example if a 20 mm final loop size is desired, it would be advantageous to begin with a thread having a length of about 6 inches (152.4 mm), and to configure the button and thread such that the middle section is 35 mm in length and the save tail section is 40 mm in length. Loop size is measured from the largest inner diameter of the fiber 1 loop. More specifically, according to a preferred embodiment, it can be the distance from the inner perimeter of the button 4 to the inner perimeter of the second stitch 20, as defined by the bracket 24 in FIG. 12. The largest inner diameter is the distance used to designate the loop size regardless if the second stitch is positioned opposite from the button or not present in the fiber loop 1 at all.

TABLE 1

| Loop Size (mm) | Fiber Length (in) | Save Tail Length (mm) | Middle Section Length (mm) | Pre-Stretch Length (mm) |
|---|---|---|---|---|
| 15 | 6 | 40 | 30 | ~13 |
| 20 | 6 | 40 | 35 | ~18 |
| 25 | 7 | 40 | 45 | ~23 |
| 30 | 8 | 45 | 60 | ~28 |
| 35 | 8 | 50 | 65 | ~33 |
| 40 | 10 | 55 | 75 | ~38 |

As shown in FIG. 2, the fiber 1 is preferably fluffed at the entry 5 and exit 6 points to make it easier for a lacing tool 7 (FIG. 3) to be inserted through the middle section 9. One end of the lacing tool 7 can include a handle to allow a user to position, guide, push, and pull the tool. The lacing tool 7 also includes a main body that is preferably substantially linear and having a diameter, or cross-section, small enough to thread through the fiber 1. The end of the lacing tool 7 opposite of the handle can include a hinged barb 10 (FIG. 3) to allow for coupling to the fiber 1. The hinge allows the barb 10 to have a lower profile when traversing through the inside of fiber 1 while minimizing the chance of snags. Other means for coupling to the fiber are readily contemplated and can nonexclusively include one or more barbs (hinged or unhinged) hooks, clamps (such that can be opened and closed by the handle) and the like, for example. Said means for coupling 10 preferably should not prevent or hinder the lacing tool 7 from being pushed into or pulled out of the inside of the fiber 1.

As depicted in FIG. 3, once the middle section 9 is defined, the barb 10 of the lacing tool 7 is pushed into the lumen of the fiber 1 at the fluffed entry point 5. The barb 10 is pushed through the inside of the middle section 9 and guided outward through the fluffed exit point 6. With reference to FIGS. 4 and 5, the cut tail 2 of the ⅓ length section is then coupled to the barb 10 and configured to allow the lacing tool 7 and cut tail 2 to be pulled back into the middle section 9 at the exit point 6. The barb 10 and coupled cut tail 2 can be pulled out of the middle section 9 at the entry point 5. As shown in FIG. 6, this step results in general loop shape with the cut tail section 2 being exposed out of the fiber 1 at the entry point 5. The exposed cut tail 2 can be cut as close to the entry point 5 as possible, utilizing one or more of the following: scissors, knife, cutting instrument, thermal knife, and/or razor blade, and the like while avoiding cutting the external fiber near the entry point 5. The remaining cut tail 2 can be retracted within the lumen of the fiber through the entry point 5, as shown in FIG. 7 by any suitable method, such as by manually or mechanically stretching the loop.

One preferred method is to utilize needle holders to cinch the loop. For example, the closed jaws of needle holders or a scissor-like tool can be inserted into the loop then opened to stretch the loop. A preferred machine could be a force gauge.

Figure 7:
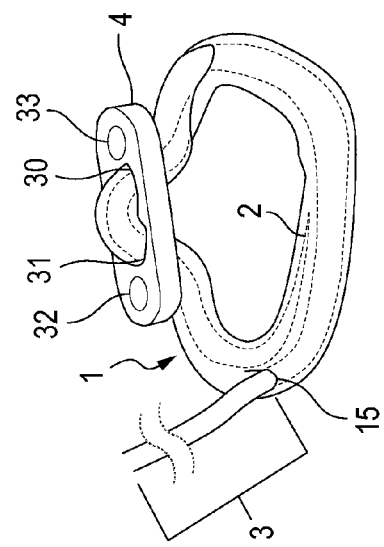
FIG. 7 is a perspective, partially internal view of the cut tail receded within the fiber.
Figure 8:
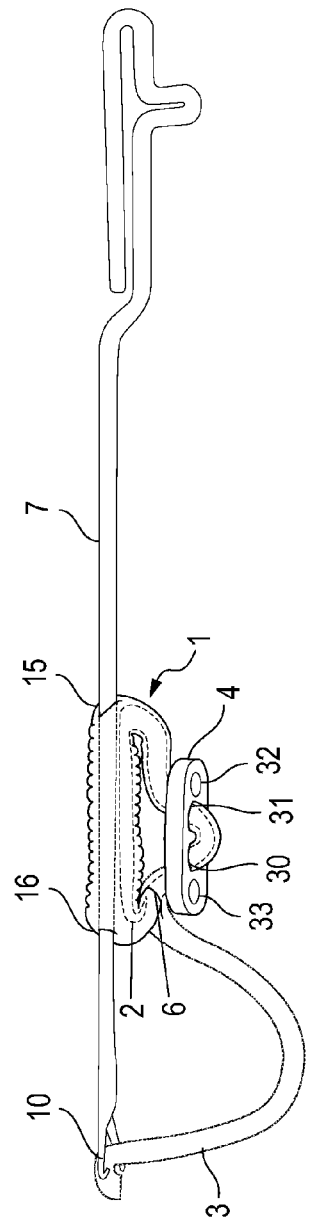
FIG. 8 is a perspective, partially internal view showing the lacing tool inserted through the fiber and grasping the save tail.

With continued reference to FIG. 7, the button 4 can be advantageously repositioned from its original position (shown in dashed lines) to a new position (shown in solid lines) at the opposite end of the loop from the original position, or approximately so. This repositioning of the button 4 advantageously allows the lacing tool 7 to traverse through the lumen of the fiber 1, as shown in FIG. 8. More specifically, second entry 15 and exit 16 points are defined along the fiber 1. The second exit point 16 can preferably be positioned within close proximity to the end of the retracted cut tail 2 to minimize the amount of external fiber outside the loop lumen while still allowing for an internal overlap, or proximity, between the save tail and cut tail 2 and 3 within the lumen. These second entry 15 and exit 16 points can also be fluffed to allow for the lacing tool 7 to readily enter and exit the fiber 1. After the second entry 15 and exit 16 points are defined, the barb 10 of the lacing tool 7 is pushed into the lumen of the fiber 1 at the fluffed second entry point 15. The barb 10 is pushed through the inside of the fiber 1 and guided outward through the fluffed second exit point 16.

Figure 9:
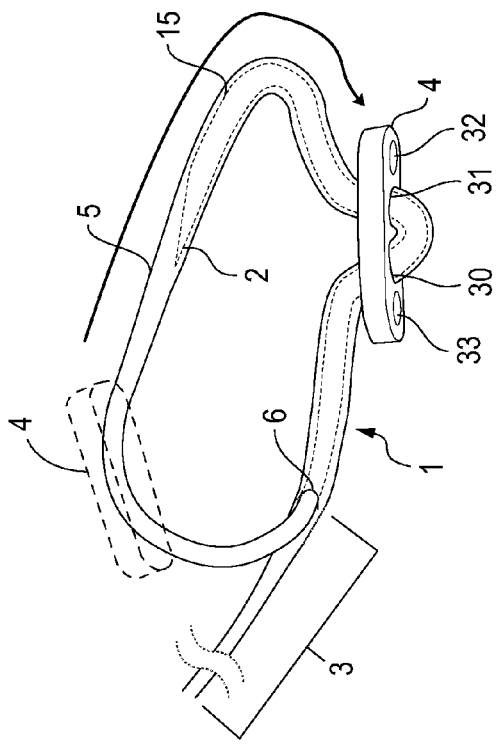
FIG. 9 is a perspective, partially internal view of the save tail extending out of the fiber.

The save tail 3 of the ⅔ section is then coupled to the barb 10 and configured to allow the lacing tool 7 and save tail 3 to be pulled back into fiber 1 at the second exit point 16. The barb 10 and coupled save tail 3 can be pulled out of fiber's lumen at the second entry point 15. As shown in FIG. 9, this step results with the save tail section 3 being exposed out of the fiber 1. The exposed save tail 3 is preferably cut near the second entry point 15, such that a small section of the save tail 3 is still exposed. Cutting can be done utilizing one or more of the following: scissors, knife, cutting instrument, thermal knife, and/or razor blade, and the like while avoiding cutting the external fiber near the second entry point 15.

After the save tail 3 is initially cut, it is preferred to manually or mechanically cinch the loop. One preferred method is to utilize needle holders to cinch the loop. For example, the closed jaws of needle holders or a scissor-like tool can be inserted into the loop then opened to stretch the loop. A preferred machine could be a force gauge. The inner diameter of the loop can be measured to determine how close it is to the final desired size. If needed, the loop can be stretched using tools or machines prior to the stitching/securing steps described below. As a preferred example, the fiber loop can be manually or mechanically stretched to approximately 100 lbs. One type of suitable machine that can be used for this step is a force gauge.

Figure 11:
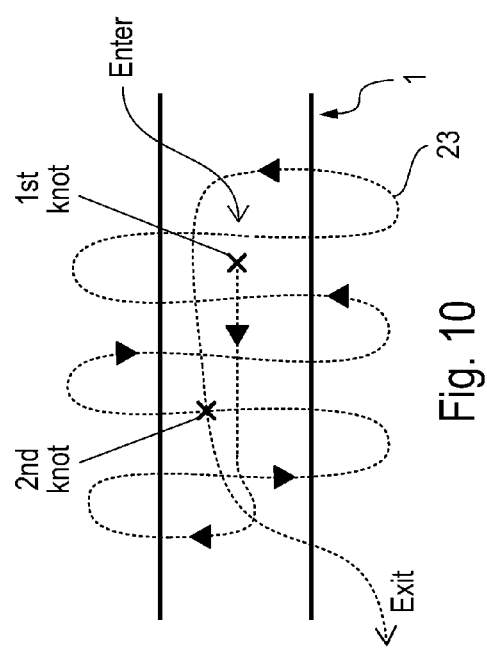
FIG. 11 is a perspective, partially internal view showing the stitching sections along the fiber.

As shown in FIG. 11, a first stitching section 21 is defined by a section on the fiber 1 that encompasses the first exit point 6 where the cut tail 2 has entered into the lumen. As shown in FIG. 11, a second stitching section 20 is defined by a section on the fiber 1 that encompasses the ends of the cut tail 2 and the save tail 3. It is important to note that the location of the first and second entry and exit points 5, 6, 15, and 16 on the fiber 1 in FIG. 11 are non-limiting, as they can be positioned closer to each other or at different locations depending on the final size of the assembly. A needle 25 and thread 23, such as UHMWPE thread, can be used to readily secure the first exit point 6 at the first stitching section 21 and the cut tail 2 and save tail 3 together at stitching section 20.

Additionally, other means for securing or reinforcing sections 20, 21, besides stitching, can also readily be used. Non-exclusive examples, of securing or reinforcing means can include one or more adhesives, such as glue, heat setting, crimping. These means can be used by themselves or in conjunction with each other, or in conjunction with stitching.

After the first section 21, having the first exit point 6 is stitched, or otherwise secured or reinforced, it is preferred to stitch or otherwise secure the second stitching section 20 where the cut tail 2 and save tail 3 overlap, or are otherwise in close proximity. According to one method, stitching using a needle 25 and thread 23, such as an UHMWPE thread, can begin below the second entry point 15, such that the stitching moves in an upward direction towards the second entry point 15 and the button 4.

Figure 10:
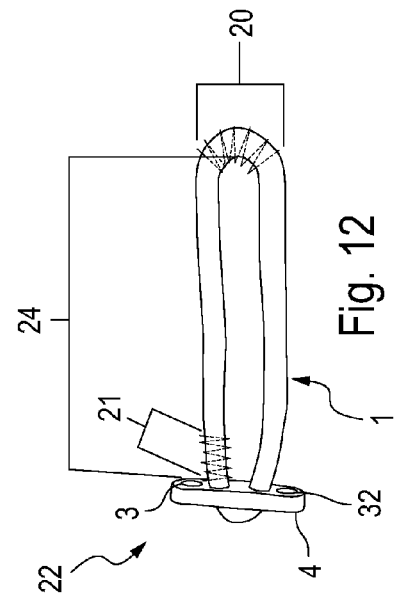
FIG. 10 is a perspective view showing a preferred directional path of stitching along the fiber.

Alternatively, and as shown in FIG. 11, the stitching or reinforcing method can be started above the final section 20 and proceed directionally away from the button 4. FIG. 10 depicts a preferred directional path of stitching along the fiber 1.

If the stitching reaches a position adjacently below or above the second entry point 15, it is preferred to cut off the remaining exposed save tail 3 as close to the second entry point 15 as possible using any suitable cutting instrument, such as a razor blade, while not cutting, and thereby compromising the fiber 1. Alternatively, this could be the first cut of the exposed save tail 3 as opposed to the second cut. The remaining save tail 3 can be retracted within the lumen of the fiber 1 through the second entry point 15 as shown in FIG. 11. The save tail 3 can be retracted into the fiber using any suitable method, such as by utilizing needle holders, as described above, or by other manual or mechanical methods of stretching the fiber loop. It is preferred that the save tail 3 is retracted within the lumen in close approximation, or on the same side of the loop, as the retracted cut tail 2. More specifically, and as shown in FIG. 11, the save tail 3 and cut tail 2 are preferably aligned adjacent to each other to create an overlap of about ⅙-¼ of an inch depending on the final loop size desired (e.g., 15-60 mm). Additionally, the ends of the cut tail 2 and save tail 3 can be adjacent to each other, or alternatively there could be a small gap between the cut tail 2 and save tail 3.

Once the save tail 3 is fully retracted within the lumen, and positioned overlapping or near the cut tail 2, it is preferred to finalize the stitching in the second section 20. Stitching, or otherwise securing, the cut tail 2 and save tail 3 together helps prevent fraying of the fiber 1. As with the first section 21, the second section 20 can be secured or reinforced utilizing other means besides thread and needle stitching. Nonexclusive examples, of securing means can include one or more adhesives, such as glue, heat setting, and/or crimping. These means can be used by themselves or in conjunction with each other, or in conjunction with stitching. According to other embodiments, the save tail 3 can first be retracted within the lumen, and then stitching or securing of the second section 20 can begin. Stitching or securing of the second section 20 advantageously secures the cut tail 2 and save tail 3 together within the braid 1 and to the braided fiber 1.

FIG. 12 depicts a preferred loop button assembly 22 after stitching or otherwise securing/reinforcing the two stitched sections 21, 20. More specifically, it is preferred to reposition the button 4 along the fiber 1, if needed, such that first stitched section 21 is positioned adjacent to, and directly below the button 4 and the second stitched section 20 is positioned on the fiber 1 at the opposite end of the assembly 22 from the button 4. This preferred configuration between the button 4 and the stitched sections 20, 21 provides advantageous tensile strength and durability, although the assembly 22 can be manipulated such that the button 4 is positioned along other locations with respect to the stitched sections 20, 21. Preferred loops of the final assembly 22 do not include a connection point that creates a figure-8 shape with a distal and proximal loop separated from each other. The final loop is preferably smooth, as one continuous strand, without significant protrusions, segmentation, divisions, and more specifically is in an ovular or circular shape.

According to certain embodiments, the assembly 22 can have only one stitched or reinforced section 20 or 21, and no more. This single reinforced section can be the section shown in 21 that covers the first exit point 6, where the cut tail 2 enters into the lumen of the fiber 1. Under this embodiment, the ends of the cut tail 2 and save tail 3 would not be connected within the lumen of the fiber 1. Alternatively, the single stitched or reinforced section can be the second section 20 that encompasses the cut tail 2 and save tail 3 junction within the lumen, without reinforcing the first exit point 6. Additional embodiments include having one or more of the reinforced sections 20 and 21 to be doubly stitched.

Alternative means of inserting the cut tail 2 and the save tail 3 into the lumen of the fiber 1 to achieve a similar final assembly are also readily contemplated herein. For example, a needle or other tool can be used to guide and insert the cut tail 2 and/or save tail 3 directly into the lumen of the fiber 1 without having the tool first being inserted into the lumen. According to alternative embodiments, the cut tail 2 and save tail 3 could be inserted within the lumen and left within, without having the ends first pulled out, cut, and retracted as described above. This could be done with the step of cinching/stretching out the loop, as described above. It is preferred that the cut tail 2 and save tail 3 are inserted substantially within the lumen, and not just their ends. More specifically, it is preferred that the entire circumference of the lumen, or substantially so, is occupied with either the cut tail 2 or save tail 3, or both with respect to overlapping between the two.

It is preferred that the assembly 22 is re-measured and re-stretched (e.g., at approximately 100 lbs.) if needed to achieve the final desired loop size.

Working Examples

Cyclic load testing was performed on various loop button assemblies manufactured according to the teachings herein. More specifically, four different types of loop button assemblies were made: (a) an assembly having a single stitched section covering the entry point of the cut tail into the lumen and positioned below the button (corresponding to section 21), (b) an assembly having a single stitched section connecting the cut tail and the save tail within the lumen, opposite of the button, (corresponding to section 20), (c) an assembly having two stitched sections, a first covering the entry point of the cut tail into the lumen and a second connecting the cut tail and the save tail within the lumen, opposite of the button (corresponding to section 21 and 20), and (d) an assembly having only one stitched section covering the entry point of the cut tail into the lumen and positioned below the button (corresponding to section 21), with said section being doubly stitched. The final fiber of the tested assemblies had a 15 mm circumference.

The loop button assemblies were coupled to an INSTRON® automated mechanical tension testing machine configured to apply cyclical mechanical stress (i.e, pulling) on the assemblies to test for tensile strength. After a cycle count of 1,000, with an average load of 1,012 N and a load at maximum tensile extension of 1,018 N, fiber loop (c) remained intact and unbroken. Applicants then tested a new 15 mm (c) loop button assembly, constructed in the same manner as the previous assembly described above, to establish a failure point. The loop broke after a cycle count of 3,987, with an average load of 1,013 N, and a load at maximum tensile strength of 1,020 N. A second (d) loop was tested and broke after a cycle count of 4,943. The (a), (b), and (d) loop assemblies were tested similarly and broke after the following cycle counts (a): 2,872, (b): 3,529 and (d): 5,098.

A comparison was made with a market leading loop button assembly, a 15 mm ENDOBUTTON® available from SMITH & NEPHEW®. In contrast to the loop button assemblies made according to the teachings herein, the thread of the ENDOBUTTON® broke after only a cycle count of 27, with an average load of 865 N and a load at maximum tensile extension of 1,005 N.

These tests established that the assemblies made according to the teachings provided herein were substantially stronger than a market leading loop button assembly.

All references listed herein are expressly incorporated by reference in their entireties. The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

What is claimed is:

1. An implantable continuous loop assembly, comprising:
   (a) a closed loop of braided fiber having a lumen and a first tail end that is threaded into the lumen at a first position to create an overlapped loop and a second tail end that is threaded into the lumen; and
   (b) a first reinforced section of fiber covering the first position where the first tail end is threaded into the lumen, said section being reinforced so as to keep said first tail in place within said lumen and a second reinforced section of fiber that couples the first and second tail ends together, and maintains the first and second tail ends in place, within the lumen.

2. The implantable continuous loop assembly of claim 1, wherein the first and second reinforced sections are stitched.

3. The implantable loop assembly of claim 1, further including a button having an aperture, and wherein the loop is threaded through the aperture.

4. The implantable loop assembly of claim 3, wherein the button has an additional aperture, and wherein the loop is threaded through the second aperture, in addition to the first aperture.

5. The implantable loop assembly of claim 3, wherein the button has a first major surface and a second major surface opposed to the first major surface and wherein said first and second apertures extend from the first major surface to the second major surface and wherein the loop is threaded from the first major surface to the second major surface through the first aperture and then back to the first major surface through the second aperture.

6. The implantable continuous loop assembly of claim 1, further including a button having an aperture, and wherein the loop is threaded through the aperture and the button is positioned adjacently above the first reinforced section of the loop and at the opposite end of the loop from the second reinforced section.

7. The implantable continuous loop assembly of claim 1, wherein the first tail and the second tail occupy the entire circumference of the loop's lumen.

8. The implantable continuous loop of claim 1, wherein the fiber is braided ultra-high molecular weight polyethylene.

9. An implantable continuous loop assembly, comprising:
(a) a closed loop of braided fiber having a lumen and a first tail end that is threaded into the lumen at a first position to create an overlapped loop and a second tail end is also threaded into said lumen; and
(b) a first reinforced section of fiber fixing the first tail end and the second tail end within the lumen, at a second position, separate from the first position.

10. The implantable continuous loop assembly of claim 9, wherein said first and second tail ends overlap within said lumen.

11. The implantable continuous loop assembly of claim 9, wherein the first reinforced section is stitched, so that the first and second tail ends are stitched together, within the lumen.

12. The implantable continuous loop assembly of claim 11, further including a second reinforced section, at the first position, where the first tail end is threaded into the lumen, the second reinforced section also acting to retain the first tail in position within the lumen.

13. The implantable loop assembly of claim 12, further including a button having two apertures, and wherein said loop is threaded through each of the two apertures.

14. The implantable continuous loop assembly of claim 13, wherein the button is positioned adjacently above the first reinforced section of the loop and at the opposite end of the loop from the second reinforced section.

15. The implantable continuous loop assembly of claim 13, wherein the button includes two additional apertures, through which the loop does not pass.

16. The implantable continuous loop assembly of claim 12, wherein the second reinforced section is reinforced through stitching.

17. An implantable continuous loop assembly, comprising:
(a) a closed loop of braided fiber having a lumen and a first tail end that is threaded into the lumen at a first position to create an overlapped loop and a second tail end is also threaded into the lumen at the first position;
(b) a first reinforced section of fiber covering the first position where both the first tail end and the second tail end are threaded into the lumen, the section being reinforced so as to keep the first tail and the second tail in place within the lumen.

18. The implantable continuous loop assembly of claim 17, wherein the first reinforced section is stitched.

19. The implantable loop assembly of claim 17, further including a button having an aperture, and wherein the loop is threaded through the aperture.

20. The implantable loop assembly of claim 19, wherein the button has an additional aperture, and wherein the loop is threaded through the second aperture, in addition to the first aperture.

21. The implantable loop assembly of claim 20, wherein the button has a first major surface and a second major surface opposed to the first major surface and wherein said first and second apertures extend from the first major surface to the second major surface and wherein the loop is threaded from the first major surface to the second major surface through the first aperture and then back to the first major surface through the second aperture.

22. The implantable continuous loop assembly of claim 17, further including a button having an aperture, and wherein the loop is threaded through the aperture and the button is positioned adjacently above the first reinforced section of the loop.

23. The implantable continuous loop assembly of claim 17, wherein the first tail and the second tail occupy the entire circumference of the loop's lumen.

24. The implantable continuous loop of claim 17, wherein the fiber is braided ultra-high molecular weight polyethylene.

* * * * *